(12) United States Patent
Hauch et al.

(10) Patent No.: US 11,173,498 B2
(45) Date of Patent: Nov. 16, 2021

(54) APPARATUS AND METHOD FOR THE ANALYSIS; ISOLATION AND/OR ENRICHMENT OF TARGET STRUCTURES IN A FLUID SAMPLE

(71) Applicant: Adnagen GmbH, Langenhagen (DE)

(72) Inventors: Siegfried Hauch, Hannover (DE); Jens Van De Flierdt, Langenhagen (DE); Nathalie Feniuk, Hannover (DE)

(73) Assignee: Adnagen GmbH, Langenhagen (DE)

( * ) Notice: Subject to any disclaimer, the term of this patent is extended or adjusted under 35 U.S.C. 154(b) by 374 days.

(21) Appl. No.: 15/542,606

(22) PCT Filed: Jan. 13, 2016

(86) PCT No.: PCT/EP2016/050500
§ 371 (c)(1),
(2) Date: Jul. 10, 2017

(87) PCT Pub. No.: WO2016/134870
PCT Pub. Date: Sep. 1, 2016

(65) Prior Publication Data
US 2018/0264483 A1 Sep. 20, 2018

(30) Foreign Application Priority Data
Feb. 24, 2015 (EP) .................................... 15156335

(51) Int. Cl.
*B03C 1/01* (2006.01)
*B03C 1/033* (2006.01)
(Continued)

(52) U.S. Cl.
CPC .............. *B03C 1/01* (2013.01); *B03C 1/0332* (2013.01); *B03C 1/288* (2013.01);
(Continued)

(58) Field of Classification Search
CPC ......... B03C 1/01; B03C 1/0332; B03C 1/288; B03C 2201/18; B03C 2201/22; B03C 2201/26; G01N 33/54326; G01N 33/54333
See application file for complete search history.

(56) References Cited

U.S. PATENT DOCUMENTS 6,036,857 A 3/2000 Chen et al.
6,514,416 B1 2/2003 Harradine et al.
(Continued)

OTHER PUBLICATIONS

The Editors of Encyclopedia Britannica, "Magnetic pole", Encyclopedia Britannica, Encyclopedia Britannica, Inc. Nov. 23, 2018.*
(Continued)

*Primary Examiner* — Benjamin L Lebron
(74) *Attorney, Agent, or Firm* — Rankin, Hill & Clark LLP

(57) ABSTRACT

The apparatus comprises a lateral arrangement of a plurality of magnetic elements, wherein at least two, more than two or all magnetic elements are arranged adjacent to each other, a flow-through tube wherein the magnetic axes of the at least two magnetic elements of the arrangement are almost or fully parallel to each other and almost or fully perpendicular to the plane of the arrangement, wherein magnetic poles of neighbouring magnetic elements, which magnetic poles are arranged directly adjacent to each other parallel to the plane of the arrangement, have different polarities. The arrangement and the tube are movable relative to each other such that the arrangement and the tube can be approached to and/or detached from each other. When the tube is approached to the arrangement, it is at least partially arranged along at least two magnetic elements.

12 Claims, 5 Drawing Sheets

(51) Int. Cl.
   *B03C 1/28* (2006.01)
   *G01N 33/543* (2006.01)
(52) U.S. Cl.
   CPC .... *G01N 33/54326* (2013.01); *B03C 2201/18* (2013.01); *B03C 2201/22* (2013.01); *B03C 2201/26* (2013.01)

(56) References Cited

U.S. PATENT DOCUMENTS

| | | |
|---|---|---|
| 2005/0202573 A1 | 9/2005 | Koyata et al. |
| 2010/0068764 A1* | 3/2010 | Sista .................. B01L 3/50273 435/79 |
| 2011/0137018 A1 | 6/2011 | Chang-Yen et al. |
| 2012/0115167 A1 | 5/2012 | Chandler et al. |
| 2013/0271250 A1 | 10/2013 | Weissleder et al. |

OTHER PUBLICATIONS

Hoshino, Kazunori et al., "Microchip-Based Immunomagnetic Detection of Circulating Tumor Cells", Lab on a Chip, Jan. 2011, pp. 3449-3457, vol. 11 No. 20, Royal Society of Chemistry, United Kingdom.

* cited by examiner

APPARATUS AND METHOD FOR THE ANALYSIS; ISOLATION AND/OR ENRICHMENT OF TARGET STRUCTURES IN A FLUID SAMPLE

The present application concerns an apparatus and a method for the isolation/or enrichment of target structures in a fluid sample. Such an apparatus and method are in particular relevant in the field of biochemistry and medicine, where target structures like biological cells or pathogens, viruses, bacteria or fungi, antibodies, antigens, peptides, proteins, pharmaceutical substances, chemical substances, RNA, DNA etc. need to be enriched, purified and/or analysed.

Magnetic bead based enrichment and purification solutions are widely used, such like immunomagnetic cell enrichment from liquid specimens or the purification of nucleic acids using bead bound complementary single strand nucleic acids to bind to the respective nucleic acid of interest.

Most of these methods are limited to low sample volumes, long enrichment times or restricted to certain sample pre-preparations. Existing solutions like the column based MACS (Milteny) provide a solution for these problems in cell enrichment but still lack in volume limitations or limiting sample properties, like viscosity and/or impurities that lead to column clogging etc. A flow-through system might help solving the volume limitations as well as certain sample properties.

However, the problem that will appear with such a device is the diameter and length of the flow-through tubing in relation to the flow speed and the required magnetic forces to hold the magnetic beads in the tubing during the sample flow and when rinsing the tubing with washing solutions, if necessary. If the diameter is small enough to allow neodymium magnets for the bead collection, the maximum flow rate is limited due to unwanted shear forces and, thus the time for processing of large volumes (5-100 ml) is unacceptably high. If the tubing diameter ranges between 0.5 mm and 1.0 mm the achievable flow rate (>50 µl/s) is acceptable, but solid state magnets up to a holding force of more than 7 kg/cm$^2$ are not able to attract the beads sufficiently. As a result the selection beads are partially lost during the procedure. This problem gets even more serious if the beads size is decreased which limits the use of different beads sizes for different applications.

Therefore a flow thought solution that is able to process high volumes of liquid samples of any kind combined in short processing time, e. g. 100 µl/sec, is needed.

The aforementioned problems are solved by the apparatus disclosed and claimed herein and the method disclosed and claimed herein. Further improvement of the inventive apparatus and the inventive method are also disclosed and claimed herein.

The apparatus according to the present invention is a means for the analysis and/or isolation and/or enrichment of target structures in/from a fluid sample. Possible target structures have been mentioned above and include among others target structures, which are of interest in the field of biochemistry and medicine like biological cells or pathogens, viruses or bacteria or fungi, antibodies, antigens, peptides, proteins, pharmaceutical substances, chemical substances, RNA, DNA etc and mixtures thereof.

The inventive apparatus comprises a lateral arrangement of a plurality of magnetic elements. These magnetic elements may be spaced by a maximum gap of ≤1 mm, preferably ≤0.5 mm, preferably ≤0.01 mm or have no space between each other.

Thus, more than two or more magnetic elements of this lateral arrangement are arranged adjacent to each other.

Further a flow-through tube may be provided, in order to flow through this flow-through tube a fluid, which comprises said target structures, e. g. bound to magnetic particles like magnetic beads. The flow-through tube may have a wall thickness WD of 0.01 mm≤WD≤0.2 mm.

In that latter arrangement of magnetic elements the magnetic axes of the at least two magnetic elements, which are adjacent to each other, are almost or fully parallel to each other and almost or fully perpendicular to the plane of the arrangement. Here and in the following the term "almost" means that the deviation from the respective property or valve is less than 10%, preferably less than 5%. E. g. for a parallel arrangement of two parallel axes with an angle of 0°, the term "almost parallel" allows these axes to be inclined to each other by 81° (10% of 90°).

Thus, on the upper surface of the arrangement the end poles of the adjacent magnetic elements adjoin each other. It is preferable, if all ends of the magnetic elements within one lateral arrangement together build a flat or almost flat surface of that arrangement.

Further, the magnetic poles of neighbouring elements, which are neighbouring to each other, have preferably different polarities. For example, in a rectangular arrangement of magnetic elements, which has lines and columns of magnetic elements, magnetic elements arranged along a line or magnetic elements arranged along a column have alternating poles on the surface of the lateral arrangement.

Furthermore, in the inventive apparatus the arrangement of the magnetic elements on the one hand and a flow-through tube on the other hand are movable relative to each other, e. g. can be approached to each other and/or detached from each other.

The flow-through tube further, if approached to the arrangement of magnetic elements, at least partially is arranged along two magnetic elements, several magnetic elements or all magnetic elements, in particular arranged along a line or along a column of magnetic elements. It is possible that the flow-through tube either is arranged such that it crosses each end of the magnetic elements on a top end in the centre of the end face of the magnetic elements. Alternatively, the flow-through tube may be arranged along the area, where neighbouring lines of magnetic elements or neighbouring columns of magnetic elements face each other.

In the inventive apparatus the surface of one, several or each of the magnetic elements, which surfaces together build the surface of the array, which is oriented towards the flow-through tube are flat, preferably flat parallel to the plane of the array or may have a convex shape or a concave shape.

The apparatus according to the present invention may further comprise a driving means to move the flow-through tube or the arrangement of magnetic elements or the flow-through tube and the arrangement of the magnetic elements.

The apparatus according to the present invention may further comprise means to flow a fluid, preferably a liquid, through the flow-through tube.

The apparatus according to the present invention may further comprise a controlling means for controlling the movement of the arrangement of magnetic elements and/or for controlling the driving means and/or for controlling the means to flow a fluid.

A corresponding method for the isolation and/or enrichment and/or analysis of target structures in a fluid sample is disclosed and claimed herein.

With the present invention it was found that surprisingly the strongest attraction of magnetic particles e. g. paramagnetic beads to the surface of the lateral arrangement of magnetic elements was observed at the edges of each individual single magnet, even if it is assumed that especially in this regions the magnetic forces are rather eliminated due to the close contact of the south pole of one magnetic element to the north pole of the neighbouring magnetic element.

With the inventive apparatus and the inventive method, thus a very sensitive and very specific method and apparatus for the analysis and/or isolation and/or enrichment of target structures is provided, where further a high volume of fluid sample can be treated in a very short time with still very high specificity of analysis and/or isolation and/or enrichment of the target structures. A preferable embodiment of the present invention uses magnetic beads suspended in a fluid, as are commercially available since long times, in order to bind the target structure first and then bind the magnetic beads to the arrangement/array of magnetic elements.

In order to bind said magnetic beads to the arrangement of magnetic elements, the magnetic elements and the flow-through tube are moved close to each other. In order to release the magnetic beads inside of the flow-through tube for collection of the magnetic beads the arrangement of magnetic elements and the flow-through tube are detached from each other and moved to different places. Thus, the magnetic force of the magnetic elements, which bind the magnetic beads, is removed from the flow-through tube. Alternatively, the magnetic beads may be contacted with a release fluid, e.g. a lysate fluid which effects release of the target structure(s) and/or of at least a part of the target structures. Further, for improved isolation of target-loaded magnetic beads, after flowing of the sample through the flow-through tube, the magnetic forces on the beads may be released once or several times, optionally under flowing a liquid back and forth in the flow-through tube before applying the magnetic forces again.

Of course, the inventive method and the inventive apparatus can also be used with any other suitable magnetic structure, not only by magnetic beads.

In the following, embodiments of the present invention are provided. Therein, features, which may be compulsory or optional, are shown in the same embodiments. However, they may also be implemented in not mentioned embodiments separately from each other.

FIG. 1 shows an array of magnetic elements, wherein magnetic elements are arranged in lines and columns.

Figure 1:
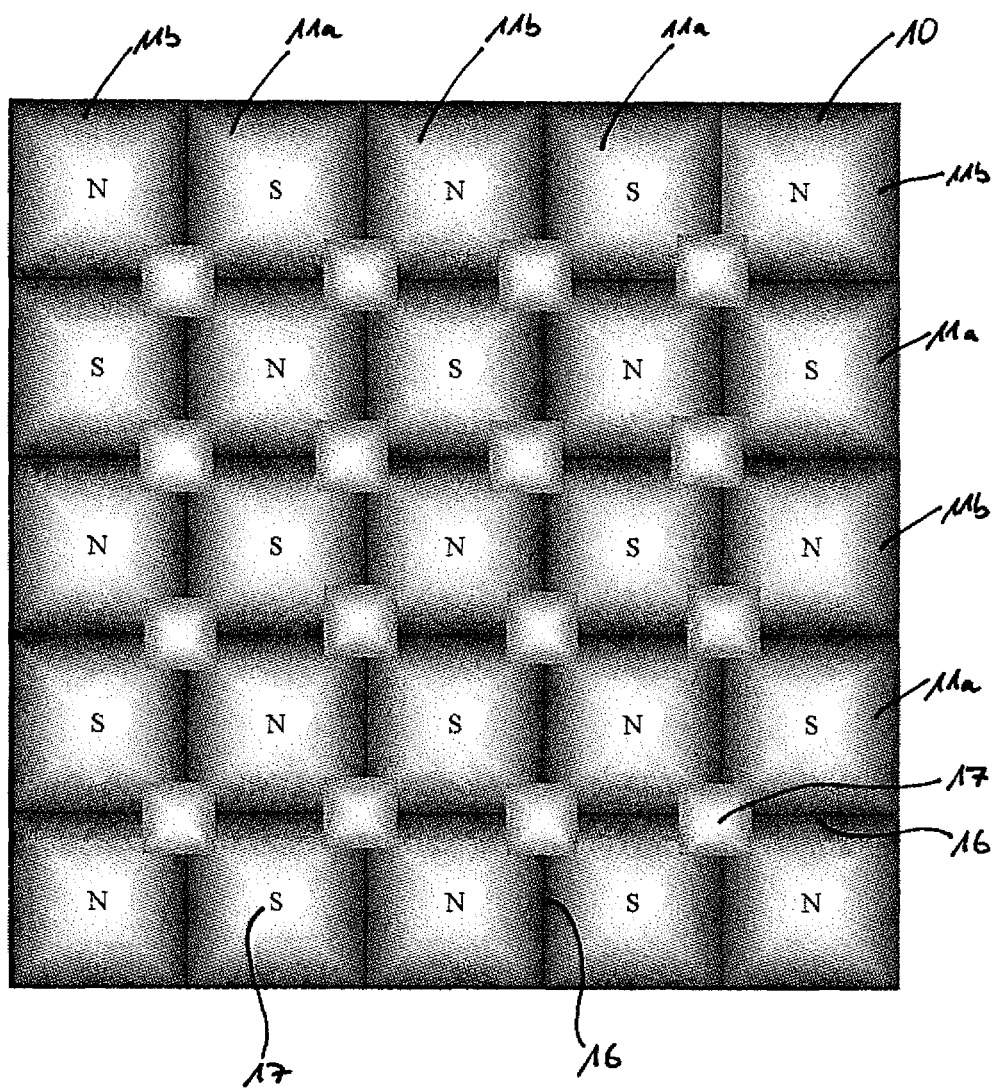
FIG. 1 shows an array of magnetic elements according to the present invention.

FIG. 1 shows a top view on the surface of a rectangular, chessboardlike arrangement 10, where 5 neighbouring magnetic elements 11a, 11b within a line and 5 neighbouring magnetic elements 11a, 11b within a column are arranged such that the polarity of their poles is alternating. Thus, a neighbouring arrangement of magnetic elements 11b with a north pole and magnetic elements 11a with a south pole is achieved. In the example in FIG. 1 the magnetic elements are arranged without any space between them, but could also be spaced to some extent.

Each of the magnetic elements 11a and 11b displays an end surface of 1 $cm^2$ and exerts a holding force of 6.5 $kg/cm^2$.

The figures show in dark areas those areas 16, where magnetic particles like magnetic beads will accumulate, whereas in the bright areas 17 less or no magnetic particles at all like magnetic beads will accumulate.

Figure 2:
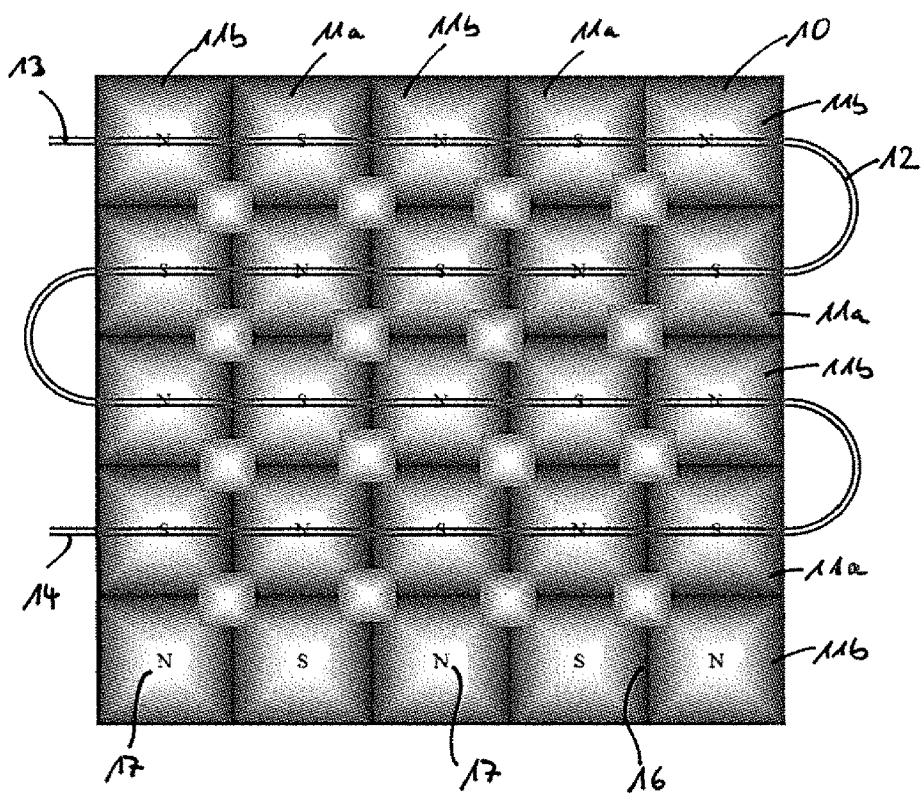
FIGS. 2 and 3 show two further arrays of magnetic elements with a flow-through tube according to the present invention.
Figure 3:
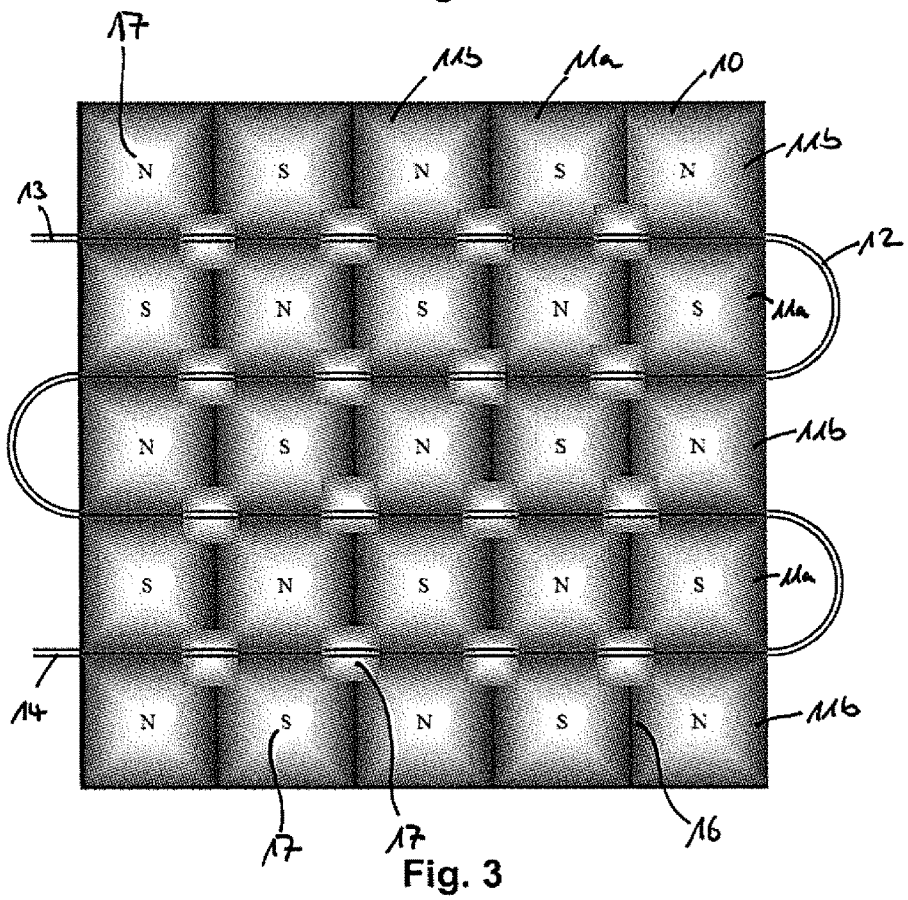

FIGS. 2 and 3 show two further arrangements 10 corresponding to the arrangement in FIG. 1. Again, the arrangement 10 of magnetic elements consists of an array of magnetic elements 11a and 11b, arranged in lines and columns. The arrangement of the magnetic elements 11a, 11b is the same as in FIG. 1 with neighbouring magnetic elements 11a, 11b in one line or neighbouring magnetic elements 11a, 11b in one column show different magnetic polarities.

In FIG. 2 and FIG. 3 two different possibilities to arrange a flow-through tube 12 on top of the shown end phases of the magnetic elements 11a, 11b of the array 10. In FIG. 2 the flow-through tube 12 runs along lines of magnetic elements 11a, 11b and crosses these magnetic elements 11a, 11b on their top end in their centre. At the end of one line the flow-through tube is bent in the way of a U-turn and then guided back over the top end centre of the end phases of magnetic elements of a neighbouring line or column. At the end of this second line again the flow-through tube is bent over, which is repeated in total three times. By this arrangement the flow-through tube 12 runs across a high number of magnetic elements from its inlet 13 to its outlet 14.

In FIG. 3 the flow-through tube 12 is arranged to run along the bordering line between different lines of magnetic elements 11a, 11b. If there is a gap between neighbouring magnetic elements of neighbouring lines, the flow-through tube may be arranged above, along or even through the inside of these gaps.

Due to the strong holding of magnetic particles by the inventive arrangement of magnetic particles, the flow-through tube may have an inner diameter of up to and more than 5 mm.

As shown by these examples, the current invention provides a solution for magnetic bead collection from sample volumes 5 ml and at high flow rates. For this purpose a magnet array is used instead of a single solid state magnet. This array is combined with e. g. a meandering flow as shown in FIGS. 2 and 3 through tubing (0.5 mm-1.0 mm inner diameter; 0.1 mm-0.2 mm wall strength) that allows high flow rates and large sample volumes.

The invention is based on the surprising finding, that surprisingly an array of small magnets (1.0 $cm^2$ each; 6.5 $kg/cm^2$) arranged in alternating polarities, even if the overall magnetic force in 2 cm distance was by far weaker than with the use of a much stronger single magnet with increased thickness, was able to attract the beads very efficiently during flow-through of the sample if the tubing was placed directly on the magnet array surface. Interestingly we found that the strongest attraction of the paramagnetic beads was observed at the edges of each individual single magnet even if we assumed that especially in these regions the magnetic forces should be rather eliminated due to the close contact of the south to a north pole.

Figure 4:
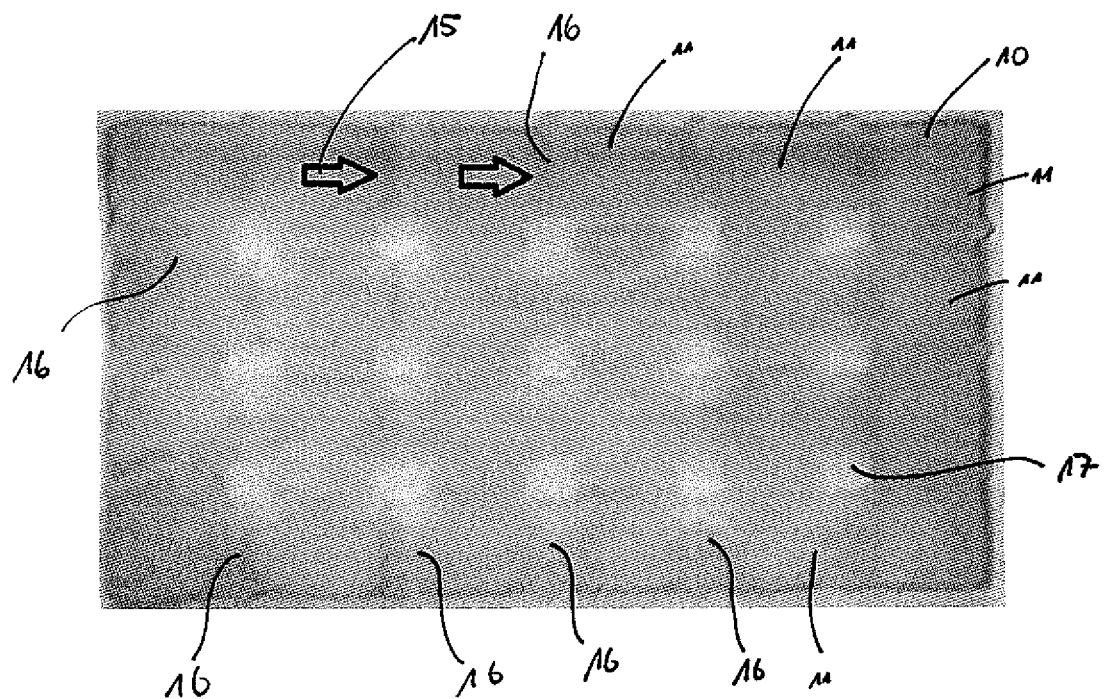
FIG. 4 shows a picture of an array of magnetic elements according to the present invention.

FIG. 4 shows a picture of an array of 6×4 magnetic elements arranged in lines and columns much like the arrangements shown in FIGS. 1 to 3, which, however, have been arrangements of 5×5 magnetic elements.

On top of this arrangement of magnetic elements in FIG. 4 a petri dish has been placed where magnetic beads (Dynabeads® Sheep anti-Mouse IgG) suspended in phosphate buffered saline have been placed. It is obvious that the magnetic beads accumulated in the darker regions, which can be found between neighboring magnetic elements.

The arrow 15 shows how the magnetic elements may be flown along a flow-through tube similar to the one displayed in FIG. 2.

Further, in order to prove efficiency of enrichment and isolation of target structures by the inventive apparatus and the inventive method a spiking experiment was conducted.

In this spiking experiment 2, 5, and 10 MCF7 breast cancer cells were spiked in duplicate into 5 ml of a healthy donor blood each subsequently followed by immunocapturing with paramagnetic beads (Dynal, Oslo, Norway, bead diameter 4.5 µm as indicated by the manufacturer) labelled with antibodies directed to epithelial antigens on MCF7 cells, which express EpCam, Muc1, as described in the manufacturer's instructions (AdnaGen GmbH, Langenhagen, Germany). In contrast to the procedure recommended in the manufacturer's instructions a flow through magnetic cell capturing and washing was investigated where the blood sample was sucked through a teflon capillary system (outer diameter 1 mm; inner diameter 0.8 mm) looping in direct contact over a magnetic array as described in FIG. 2 using a peristaltic pump (flow: 2.5 ml/min).

This experiment was designed to show, that using such a magnetic array the cells were efficiently captured in the capillaries, which could be proven by subsequent cell lysis and molecular mRNA detection of tumor cell associated markers (EpCam, Muc1, Her2) using the AdnaTest BreastCancerDetect. Results were visualized with the Agilent Bioanalyzer 2100 (FIG. 5) and analyzed for recovery according to the manufacturer's instructions.

Figure 5:
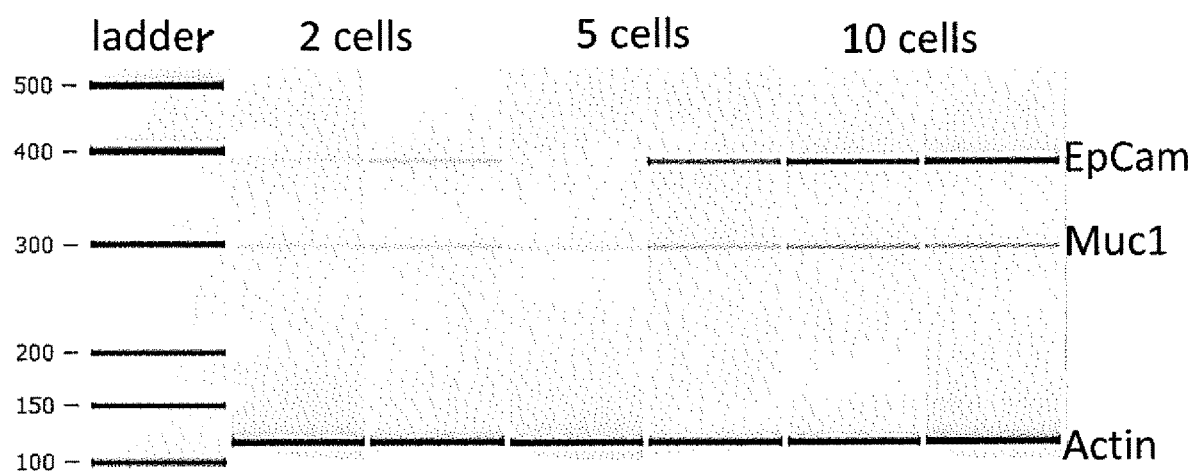
FIG. 5 shows an analysis of the separation of targets achieved by using the inventive apparatus and the inventive method.

FIG. 5 shows an analysis of the samples prepared in the spiking experiment. The first line provides a molecular marker ladder, while the second and third line show the results with two samples, where two cells of MCF7 breast cancer cells were spiked into the original sample to be analyzed. The $4^{th}$ and $5^{th}$ line show the results of the same experiment with two samples where, however, 5 cells of MCF7 breast cancer cells were spiked in the sample. The $6^{th}$ and $7^{th}$ line show the results with the independent two samples, wherein 10 cells of MCF7 breast cancer cells were spiked.

It is immediately obvious, that the tumor markers EpCam and Muc1 expressed by these cells were safely detected in almost all of these samples. Thus, the present method and the present apparatus were able to isolate two cells of MCF7 breast cancer cells from 5 ml of a healthy donor blood for detection of the tumor markers contained therein. By this result it could be demonstrated, that the flow-through capturing of immunomagnetic target cells by the present invention is efficiently realized even using high flow conditions by using a magnetic element array as in the present invention.

Figure 6:
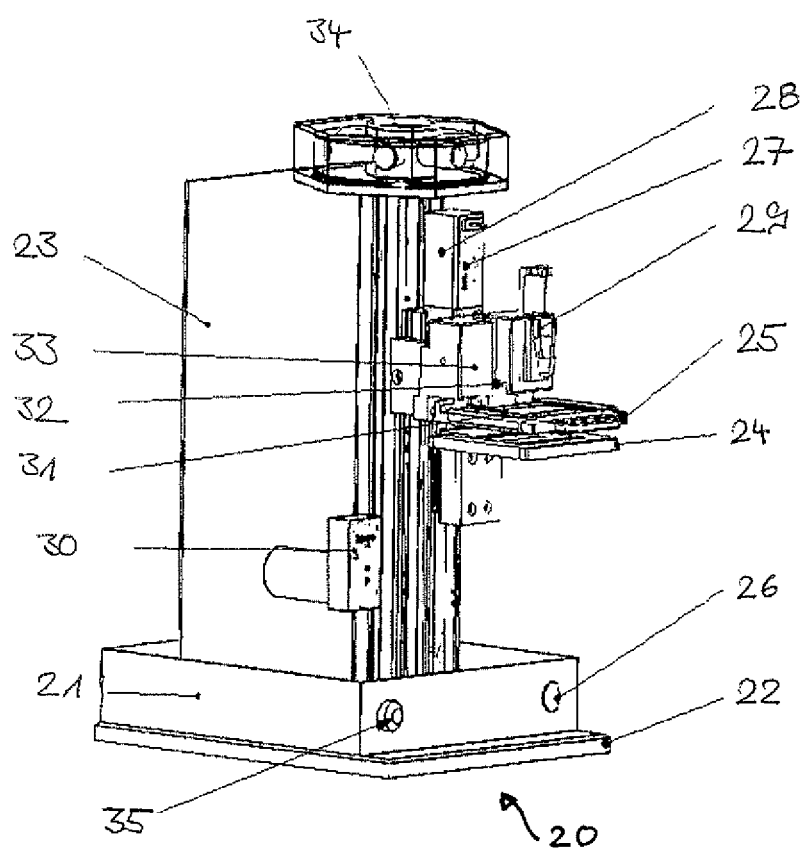
FIG. 6 shows an apparatus according to the present invention including arrangement of magnetic elements.

FIG. 6 shows a set-up, which is able to do the previously shown analysis in an automated way using the inventive arrangement of magnetic elements.

FIG. 6 shows an inventive apparatus 20 for isolating and/or enrichment and/or analysis of target structures in fluid samples with further improvements in order to provide an automated method. The apparatus 20 comprises a housing 21, where a column is built in, which holds an array 24 of magnetic elements as shown e. g. in FIGS. 1 to 3. Above that array 24 of magnetic elements a separation cartridge 25 is arranged which comprises a meandering flow-through tube. In this apparatus 20 the magnetic array 24 is moveable in order to approach the separation cartridge 25 for separation of magnetic units, e. g. magnetic beads, in the flow-through tube and in order to detach from the separation cartridge 25 in order to allow the isolated and/or enriched magnetic particles in the flow-through tube to be washed out for further analysis.

The apparatus 20 comprises a base plate 22 and a housing 21 and further build into the housing 21 a power on/off button 26 and a pump speed governor 35. This pump speed governor 35 is configured to control the speed of a peristaltic pump 30, which pumps e.g. the sample, washing fluids and the lysate. The latter is collected in a tube placed in the lysate holder 29. The sample and subsequent washing buffers are pumped through the flow-through tube in separation cartridge 25. Further elements of the apparatus 20 comprise clamping elements 31 for fixing the flow-through tube and the cover of the separation cartridge, a syringe slot 32 where the sample vessel is placed, an upper cartridge holder 33 which contains a sample-in valve, a circuit board 23 containing programmable relay switches to control the electronic valves 34, the sample-in valve and the pump as well as an actuator 27 for moving the magnetic array 24. A couple of elements are fixed to the mounting bar 28.

By this apparatus 20 it is possible, to first move the magnetic array 24 close to the separation cartridge 25, then flow a sample through the flow-through tube of the separation cartridge in order to accumulate in the magnetic array 24 any magnetic particles like magnetic beads, which are contained in the sample and which may specifically or nonspecifically bind target structures. Following this, in a washing step a washing liquid is flown through the flow-through tube of the separation cartridge 25 which is still in close contact or neighborhood to the array 24, in order to remove all or most remains of the sample liquid which are not magnetic particles in the flow-through tube. During this washing step, the magnetic particles, which are held in their position by the magnetic array 24 inside of the flow-through tube of the separation cartridge 25 are not removed and thus isolated.

In order to collect then the magnetic particles held by the magnetic array 24, the magnetic array 24 is moved by the actuator 27 to detach the array 24 from the separation cartridge 25. By this step the magnetic beads in the flow-through tube of the separation cartridge 25 are released from the magnetic forces of the array 24 and can then be washed out by a washing buffer flown through the flow-through tube of the separation cartridge 25.

In addition in a subsequent step the release of the target structure or of at least a part of the target structures from the magnetic beads, e.g. by applying a release fluid, can also be performed in the capillaries. Thus, the magnetically bound magnetic members (e.g. magnetic beads) may be treated such that they release the target or at least parts of the target which may then be washed out e.g. for further analysis.

The magnetic beads, which have been isolated, collected and possibly enriched by the aforementioned steps, can then be further analysed for the presence or absence of the target structure.

It is of advantage, if the magnetic particles show a specific binding to the target structure to be analysed in order to provide a sufficient collection, isolation and enrichment of the target structures.

The apparatus shown in FIG. 6 was designed to provide a fully automated solution for the immunomagnetic capturing of cells but also for other immunomagnetic accessible targets and their subsequent analysis to get, for example, access to the genetic but also protein expression target information and more. Key of the process is the software controlled movable magnetic array 24 as shown in FIG. 6 combined with electronic valves steering the sample, potential washing buffer and lysis buffer flow and more. End product of the procedure is a target enriched and/or even purified sample that can be subsequently analyzed by further profiling.

In order to test the above mentioned inventive apparatus, the above described automated apparatus and its working procedure based on the efficient capturing of immunomagnetically labelled cells under flow conditions (5-10 ml/min) in teflon capillaries (outer diameter 1 mm; inner diameter 0.8 mm) were investigated in clinical breast cancer patient blood samples and compared to the manual workflow as described in the AdnaTest BreastCancerSelect/Detect® instructions which is not using the inventive magnetic arrays in the capturing process.

For this purpose, CTCs (circulating tumor cells) were isolated from EDTA blood of 13 primary and 20 metastasized (MBC) patients with the AdnaCellector (same labelling conditions as with the manual AdnaTest BreastCancerSelect) and the manual AdnaTest BreastCancerSelect (AdnaGen GmbH, Langenhagen, Germany) in duplicates of 5 ml. The lysates generated from both selection variants were processed manually with the AdnaTest BreastCancer-Detect. Established cDNA was used for multiplex PCR (MUC-1, GA733-2, Her2). Resulting PCR fragments were analyzed with the Agilent Bioanalyzer 2100. Patients were classified as CTC positive if at least one marker was detected with a concentration≥0.15 ng/µl. Assay positivity for the blood samples from the same patient was evaluated with regard to the selection method. To further estimate the ease of use of both methods a non-experienced trainee was chosen to perform the procedure.

Comparing all clinical samples, the detection rate was 32% (20/61) for the manual workflow and 42% (25/60) using the AdnaCellector with an overall concordance of 81% (p<0.001). If samples were separately analyzed for blood from primary or metastatic patients the manual procedure detected in primary blood 35% (8/23) positive samples vs. 30% (7/23) positivity by the AdnaCellector and 33% (12/36) vs 50% (18/37) in metastatic blood samples, respectively. The overall concordance was 76% (p=0.05) in the primary setting and 86% (p<0.001) for the metastatic samples.

It can be concluded that for CTC detection in a clinical setting we were able to demonstrate a good concordance of the fully automated AdnaCellector prototype using the magnetic array as described in the present invention even at a flow rate of 5-10 ml/min in teflon capillaries with an inner diameter of 0.8 mm compared to the manual workflow of the AdnaTest BreastCancerSelect. Most interestingly, in the metastatic setting we even observed a substantial higher sensitivity vs. the manual procedure which may indicate that this automated and, therefore, standardized procedure may provide better test performance if the AdnaTest BreastCancerSelect procedure is used by non-experienced personnel.

The invention claimed is:

1. An apparatus for analyzing, isolating and/or enriching target structures in a fluid sample comprising:
   a lateral arrangement of a plurality of magnetic elements having square top ends, wherein the plurality of magnetic elements are arranged in a plurality of rows and columns such that the polarity of their respective square top ends in a plane of the arrangement alternates in a chessboard-like manner and
   a flow-through tube having an outer diameter that is less than the diameter of the square top ends of the plurality of magnetic elements in the lateral arrangement;
   wherein at least one of the arrangement and the flow-through tube is configured to be selectively movable relative to the other such that, in a drawn-together position, the arrangement and the flow-through tube are drawn toward each other, and, in a separated position, the arrangement and the flow-through tube are separated from each other, and
   wherein, when the flow-through tube and the arrangement are in the drawn-together position, the flow-through tube runs along one of the plurality of rows of the magnetic elements and crosses the magnetic elements in said row on their top end in their center and, at the end of said row, makes a U-turn bend and is guided back over another of the plurality of rows of the magnetic elements and crosses the magnetic elements in said row on their top end in their center.

2. The apparatus according to claim 1, wherein when the flow-through tube and the arrangement are in the drawn-together position, the flow-through tube crosses a gap between at least two of the plurality of magnetic elements in the arrangement.

3. The apparatus according to claim 1, wherein neighboring magnetic elements of each line and/or column adjoin each other with a maximum gap between the neighboring magnetic elements of ≤1 mm.

4. The apparatus according to claim 1, wherein the top end of at least one of the magnetic elements has a surface area of ≤5 cm$^2$.

5. The apparatus according to claim 1, wherein at least one of the magnetic elements has a holding force of ≥0.5 kg/cm$^2$.

6. The apparatus according to claim 1, wherein the flow-through tube has an inner diameter ID of 0.05 mm≤ID≤10.0 mm.

7. The apparatus according to claim 1, wherein when the flow-through tube and the arrangement are in the drawn-together position, a distance from a most protruded part of each magnetic element in the arrangement to the flow-through tube is, for each magnetic element, or for the arrangement as a whole, ≤5 mm.

8. A method for analyzing, isolating and/or enriching target structures in a fluid sample comprising:
   configuring an apparatus according to claim 1 such that the flow tube and the arrangement of magnetic elements are drawn toward each other and:
   a) loading a fluid comprising target structures with magnetic members, which are configured to specifically or unspecifically bind to said target structures,
   b) flowing the loaded fluid through the flow-through tube,
   c) optionally flowing one or more other fluids through the flow-through tube,
   d) separating the flow-through tube and the arrangement of magnetic members from each other by selectively moving at least one of the arrangement and the flow-through tube,
   e) flowing a further fluid through the flow-through tube, and
   f) optionally analyzing the further fluid flowed through the flow-through tube to determine whether said target structures are present.

9. A method for analyzing, isolating and/or enriching target structures in a fluid sample comprising:
configuring an apparatus according to claim 1 such that the flow tube and the arrangement of magnetic elements are drawn toward each other and:
a) loading a fluid comprising target structures with magnetic members, which are configured to specifically or unspecifically bind to said target structures,
b) flowing the loaded fluid through the flow-through tube,
c) optionally flowing one or more other fluids through the flow-through tube,
d) flowing a release fluid through the flow-through tube for releasing the target structures and/or at least parts of the target structures from the magnetic members, and
e) optionally analyzing the released target structure(s) and/or the released part(s) of the target structures.

10. The method according to claim 9, wherein
a) the target structures are biological cells or pathogens, and/or
b) the magnetic members are paramagnetic beads, and/or
c) the magnetic members have a maximum diameter MD of 5 nm≤MD≤20 µm.

11. An apparatus for analyzing, isolating and/or enriching target structures in a fluid sample comprising:
a lateral arrangement of a plurality of magnetic elements having square top ends, wherein the plurality of magnetic elements are arranged in a plurality of rows and columns such that the polarity of their respective square top ends in a plane of the arrangement alternates in a chessboard-like manner; and
a flow-through tube having an outer diameter that is less than the diameter of the square top ends of the plurality of magnetic elements in the lateral arrangement;
wherein at least one of the arrangement and the flow-through tube is configured to be selectively movable relative to the other such that, in a drawn-together position, the arrangement and the flow-through tube are drawn toward each other, and, in a separated position, the arrangement and the flow-through tube are separated from each other, and
wherein, when the flow-through tube and the arrangement are in the drawn-together position, the flow-through tube runs along a bordering row between two different rows of the plurality of rows of the magnetic elements and, at the end of said bordering row, makes a U-turn bend and is guided back over another bordering row between another two different rows of the plurality of rows of the magnetic elements.

12. The apparatus according to claim 11, wherein when the flow-through tube and the arrangement are in the drawn-together position, the flow-through tube is arranged along a gap between neighboring magnetic elements in the two different rows of the plurality of rows of the magnetic elements that form the bordering row.

* * * * *